United States Patent [19]

Kuzmak

[11] Patent Number: 5,074,868

[45] Date of Patent: Dec. 24, 1991

[54] REVERSIBLE STOMA-ADJUSTABLE GASTRIC BAND

[75] Inventor: Lubomyr I. Kuzmak, Livingston, N.J.

[73] Assignee: INAMED Development Company, Carpinteria, Calif.

[21] Appl. No.: 562,391

[22] Filed: Aug. 3, 1990

[51] Int. Cl.$^5$ ............................................. A61B 17/00
[52] U.S. Cl. .................................... 606/157; 606/228
[58] Field of Search ................ 606/151, 153, 157, 228

[56] References Cited

U.S. PATENT DOCUMENTS 4,416,267 11/1983 Garren et al. .
4,592,339 6/1986 Kuzmak et al. .
4,696,288 9/1987 Kuzmak et al. .
4,983,177 1/1991 Wolf ..................................... 606/157

*Primary Examiner*—Randy Citrin Shay
*Assistant Examiner*—R. Clarke
*Attorney, Agent, or Firm*—Michael G. Petit

[57] ABSTRACT

A reversible gastric banding device for creating a stoma opening in the stomach for restricting food intake into the lower digestive portion of the stomach. The band is operatively placed to encircle the stomach. Once in position, it is held securely with sutures on the outside of the stomach thereby prohibiting the encircled stoma opening from expanding. If, following implantation, it becomes necessary or desirable to remove the gastric band, a remotely actuated releasing portion permits the removal of the gastric band without major surgery. In one embodiment, the banding device is conveniently removed by means of a retractable blade within the band which blade, when retracted by remote activation, severs the retaining sutures and frees the band for removal. In addition to having a remotely actuated releasing portion, most preferred embodiments of the device includes a flexible substantially non-extensible band portion having an expandable, balloon-like section that is in fluid communication with a remote injection site. The expandable section is used to adjust the size of the stoma opening.

8 Claims, 4 Drawing Sheets

REVERSIBLE STOMA-ADJUSTABLE GASTRIC BAND

BACKGROUND OF THE INVENTION

1. Field of the Invention

The present invention relates to a device for the treatment of morbid obesity and, in particular, it relates to a reversible gastric banding device that encircles and compresses a portion of the stomach to form a stoma opening of reduced diameter, the reversible feature permitting removal of the device without the necessity of major surgery.

2. Definitions

"Reversible gastric band" as used herein, shall mean a gastric band which may be removed from an encircling position around the stomach without major surgery.

"Stoma-Adjustable gastric band" as used herein, shall mean a gastric band which may be adjusted to vary the diameter of the stoma opening within that portion of the stomach encircled by the band.

3. Description of the Prior Art

Morbid obesity is a condition that is associated with a multitude of other hazards to health that include socio-psychologic problems and reduced life expectancy. Dietary management of morbid obesity has not been successful as a long term treatment. Psychiatric or dietary regimens depend upon the willpower of the patent to achieve the desired results. While weight loss may occur, the lack of willpower in patients often leads to ultimate failure. In response to the failure of dietary management, various surgical techniques have been developed and used to try to treat morbid obesity.

Methods that have been used in the prior art to treat morbid obesity include gastric bypasses and small-bowel bypasses. Stapling of portions of the stomach has also been used to treat morbid obesity. This includes both vertical and horizontal stapling and other variations trying to reduce the size of the stomach or make a small stoma opening. Many problems have been associated with the use of staples. First, staples are undependable; second, they may cause perforations; and the pouch or stoma opening formed by the staples becomes enlarged over time making the procedure useless.

Yet another method that has been developed is the placement of an inflatable bag or balloon into the stomach causing the recipient to feel "full." This procedure has been described in the patent to Garren et al U.S. Pat. No. 4,416,267 which discloses a device which displaces volume inside the stomach thereby reducing the size of the gastric compartment and which is easily removed. The balloon is inflated to approximately 80% of the stomach volume and remains in the stomach for a period of about three months or more. This procedure, although simple, has resulted in intestinal blockage, gastric ulcers, and even in one instance, death and fails to address the problems of potentially deleterious contact with the gastric mucosa which can result from leaving an inflated bag in the stomach for an extended period of time. Moreover, it also failed to produce significant weight loss for long periods of time.

A more promising method employs the placement of a band around a portion of the stomach thereby compressing the stomach and creating a stoma opening that is less than the normal interior diameter of the stomach for restricting food intake into the lower digestive portion of the stomach. Such a band has been described by Kuzmak et al in U.S. Pat. No. 4,592,339. It comprises a substantially non-extensible belt-like strap which constrictively encircles the outside of the stomach thereby preventing the stoma opening from expanding. Kuzmak et al also describe bands which include a balloon-like section that is expandable and deflatable through a remote injection site. The balloon-like expandable section is used to adjust the size of the stoma opening both intraoperatively and post-operatively. Such a device is referred to as a stoma-adjustable gastric band. Although the banding procedure has great promise due to its simplicity and the fact that it retains the desired diameter of the stoma opening, there have been problems in obtaining a proper sized stoma opening. Kuzmak, in U.S. Pat. No. 4,696,288, describes a calibrating apparatus and method for using with a gastric banding device. The calibrating apparatus facilitates controlling the size of the stoma with the gastric band.

Complications have been observed with both inflatable and non-inflatable gastric bands. In particular, obstruction of the stoma from edema and migration of the band has been observed. Such edema-caused obstruction of the stoma may be due to excessive vomiting. In these cases, the stoma must be enlarged either by deflating the expandable portion of a band or by removing the band altogether.

Until now, following implantation, the only way to remove a gastric banding device is by major surgery. Thus, while it is possible to vary the pressure on the exterior wall of the stomach by injection or removal of fluid into or out of a remote injection port, it is necessary to perform major surgery to remove prior art gastric bands. It is desirable to provide a gastric banding device with means thereon for removal of the band without the necessity for major surgery. A gastric band with such means for removal is referred to hereinafter as a reversible gastric band.

SUMMARY OF THE INVENTION

The present invention is a reversible gastric band for creating a stoma opening in the stomach. The essential and novel feature of the invention is the means thereon for the removal of the band without the need for major surgery. Such a reversible gastric band may further include means thereon permitting remote adjustment of the stoma opening after implantation by adding or removing fluid from the expandable portion of a stoma-adjustable gastric band. For example, in a preferred embodiment, the reversible gastric band includes, in addition to means for nonsurgical removal, a flexible substantially non-extensible band portion which encircles the stomach, and has, in addition, a balloon-like expandable section that is expandable and deflatable through a remote injection site. The expandable section is used to adjust the size of the stoma opening by percutaneous injection of a fluid into, or removal of fluid from an implantable injection port, the interior chamber of which port is in fluid communication with the expandable section. With this preferred embodiment, if the patient is not losing weight as expected, the expandable section may be further expanded by injecting a fluid into the injection port thereby increasing the size of the expandable section which, in turn, compresses the stomach thereby further decreasing the size of the stoma opening. The decrease in the size of the stoma opening further restricts the flow of food into the lower digestive portion of the stomach. If the patient is receiving inadequate nutrition and the weight loss is too great, the expandable section is incrementally deflated by withdrawing fluid from the injection site, thereby increasing the size of the stoma opening and increasing the flow of food into the lower stomach portion.

The object of the invention is to provide a reversible gastric band suitable for the adjustable formation of a stoma within the stomach.

DETAILED DESCRIPTION OF THE PREFERRED EMBODIMENTS

Figure 1:
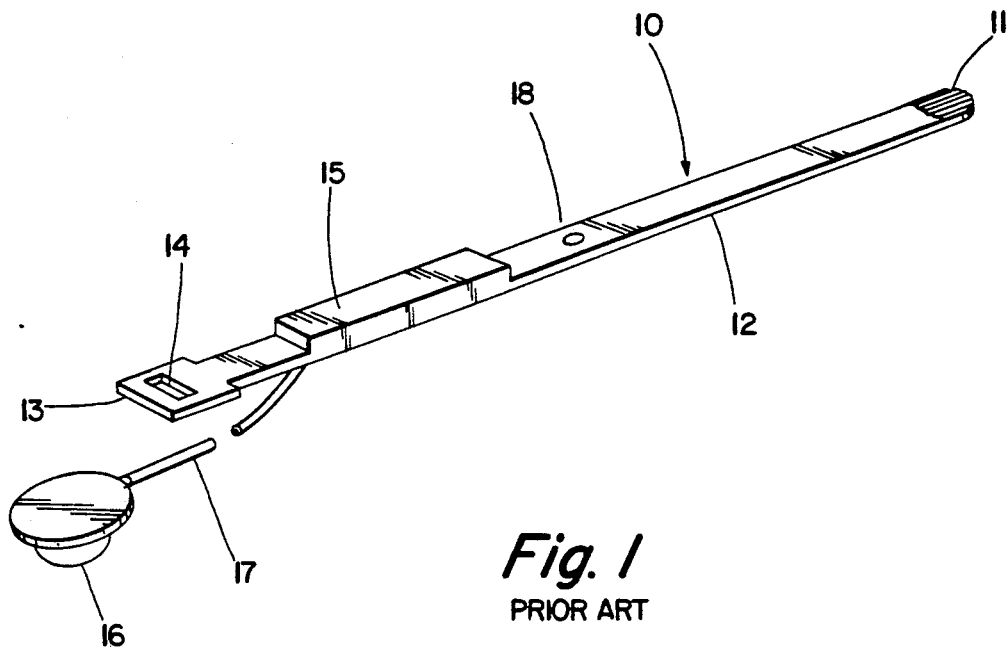
FIG. 1 is a perspective view of a prior art stoma-adjustable band.

A prior art stoma-adjustable gastric banding device is generally indicated at 10 in FIG. 1. The device includes a longitudinal substantially non-extensible band portion (12), an expandable section (15), a buckle portion (13), a guide tab portion (11), and an injection site (16) in fluid communication with the expandable section by means of tubing (17). The band portion (12) preferably includes two central layers made of a Dacron mesh material (not shown) embedded in a medical grade silicone polymer. The expandable section (15) includes an inflatable balloon made of a silicone polymer interposed between the layers. The balloon is preferably at least partially filled with a physiologically compatible fluid such as a saline solution. The balloon is inflated and deflated by piercing the injection site (16) with a hypodermic needle and either adding or withdrawing fluid. In practice, the band is wrapped around the stomach and the guide tab (11) passed through the slot (14) in buckle (13) and cinched down snugly. The loose end of the band, that is, the tab end which has passed through the slot (14), is sutured to the encircling band portion in the general area denoted as (18) thus securing the band about the stomach. Once the suture(s) are in place, the buckle may be removed. After the prior art gastric banding device (10) is in place, and the stoma adjusted, the injection site (16) may be anchored between the rectus sheaths at a convenient location and the patient allowed to recover.

In summary, the prior art device (10) provides a permanent implant that controls the amount of food ingested by a morbidly obese patient. The size of the stoma opening may be adjusted by means of percutaneous injection or withdrawal of fluid from an expandable balloon-like section without need for further surgery to regulate the flow of food within the stomach of the patient. If it is necessary, however, to remove the prior art gastric bands, major surgery is necessary.

Figure 2:
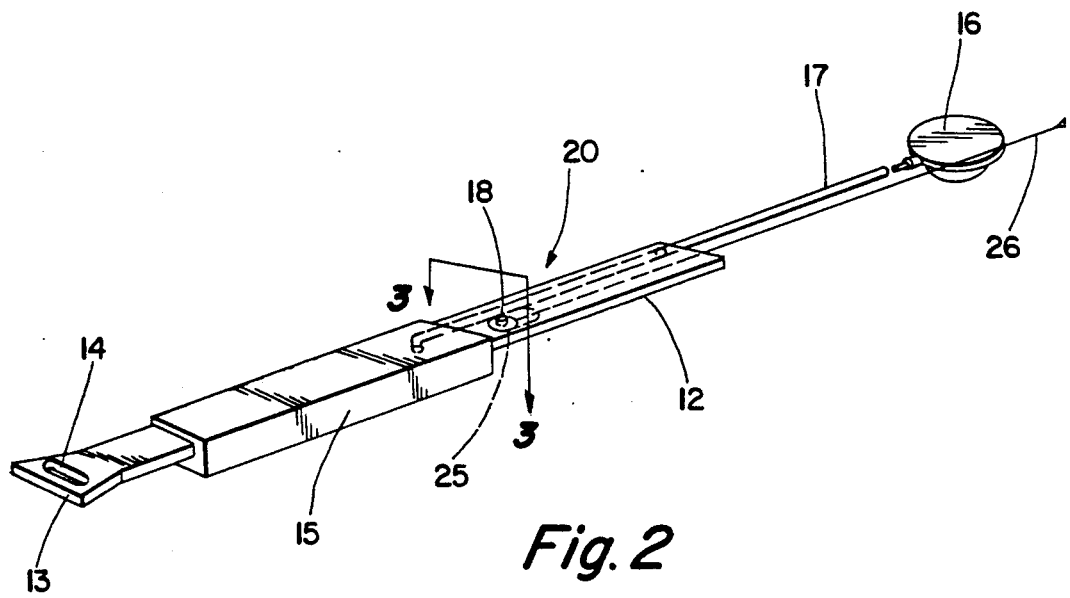
FIG. 2 is a perspective view of the reversible gastric banding device of the present invention.

Turning now to FIG. 2, we see the reversible gastric band of the present invention is generally indicated at 20 in FIG. 2. The device, although similar to the prior art device (10), includes a suture-cutting blade portion (25) and a remote blade pull-cord (26) which facilitates removal of the gastric banding device following implantation without the need for major surgery thereby endowing the prior art gastric band with reversibility.

Figure 3:
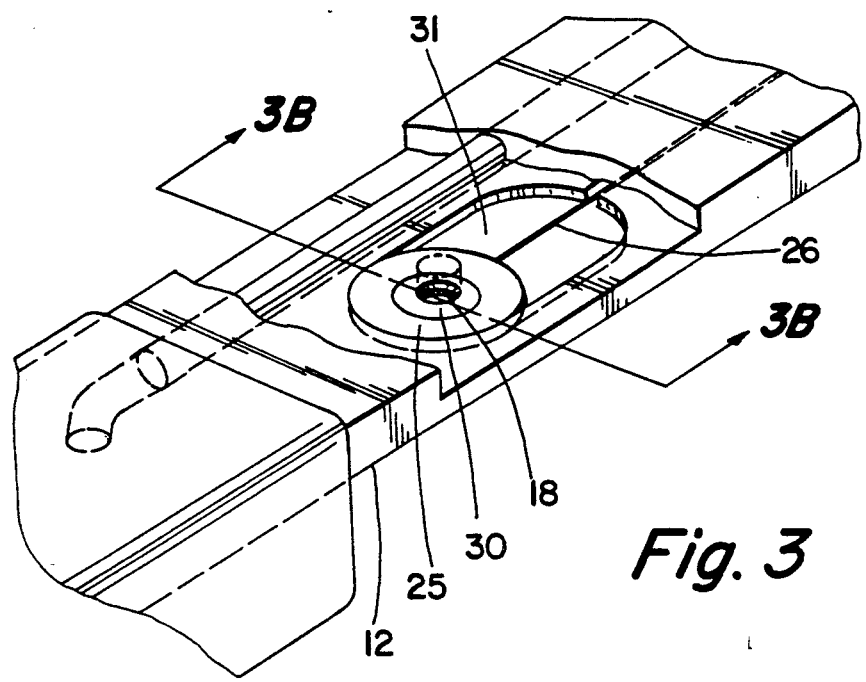
FIG. 3 A-C are exploded views of two embodiments of suture cutting means taken along line 3—3 of FIG. 2.

Directing attention now to FIG. 3A which shows a partially cutaway view of FIG. 2 taken along line 3—3, showing one preferred embodiment of the reversible gastric band in which the suture-cutting blade portion is an annular ring (25), the inner circumferential border of which is honed to a sharp cutting edge (30). The suture-cutting portion is positioned within a slot (31) to encircle a suture guide hole (18). A pull cord (26) which is attached to the blade (25) extends out of the slot (31) to emerge from the band (12) and preferably extend collinearly with the tubing used to inflate the balloon-like portion of the band, preferably and conveniently through a second lumen in double lumen tubing, to terminate adjacent the injection reservoir.

Figure 3B:
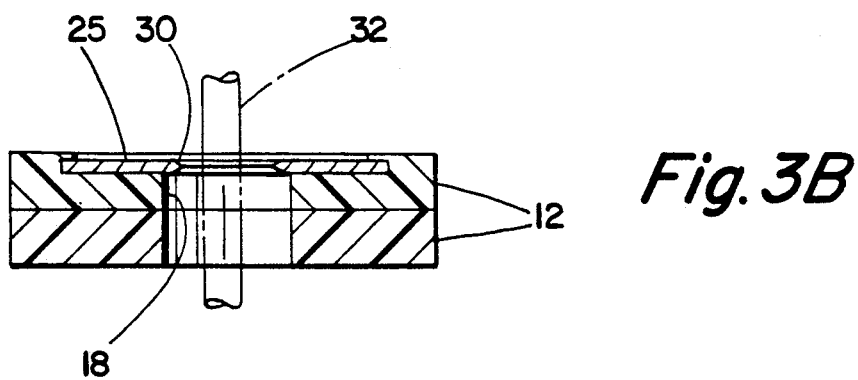

FIG. 3B shows a cutaway view of FIG. 3A along line 3B—3B in which a suture (32) is passed through the suture hole (18) to secure overlapping portions (12) of the reversible gastric band to each other. The suture (32) is tied off thereby preventing the gastric band from becoming loose following implantation.

Figure 3C:
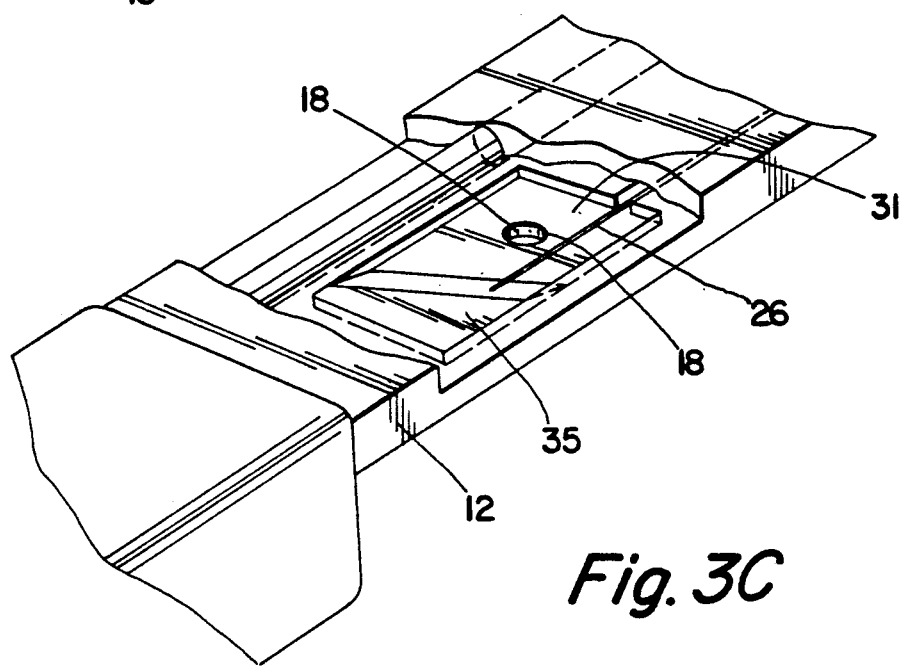

FIG. 3C shows yet another preferred embodiment of a suture-cutting blade device in which the suture hole (18) is in the path of a guillotine blade (35) with a sharp edge (36) which blade slides in the blade slot (31) in response to tension on the pull wire (26).

Figure 4A:
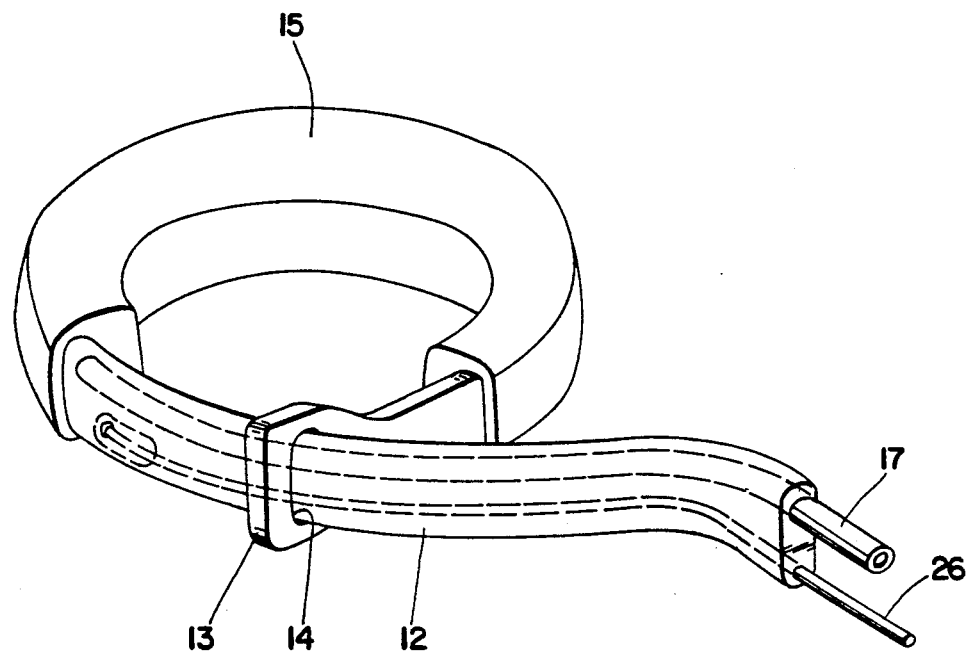
FIG. 4 A and B are perspective views of a preferred embodiment of the reversible gastric band showing the relationship of parts before being placed around the stomach.
Figure 4B:
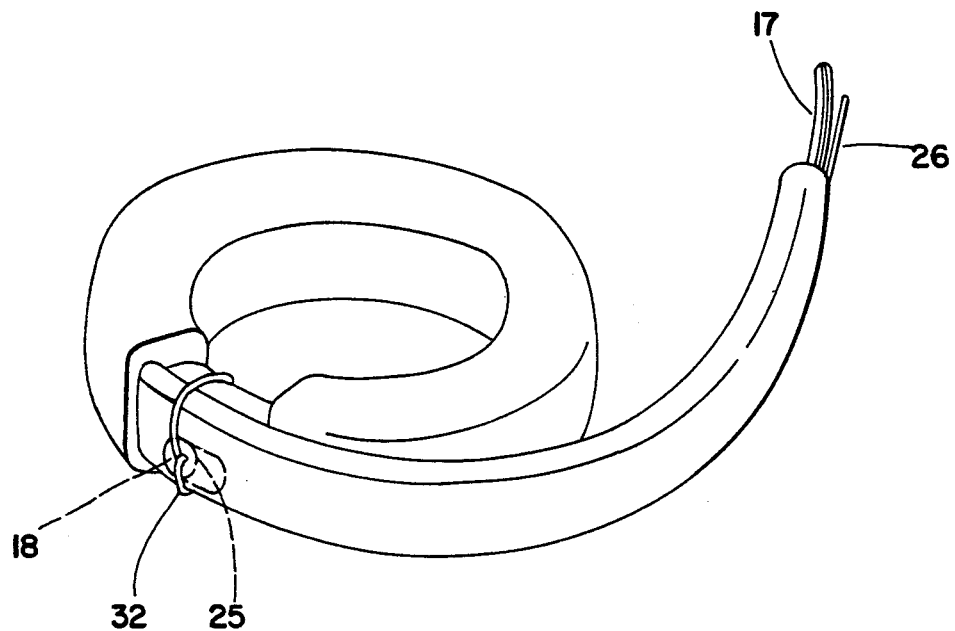
Figure 5:
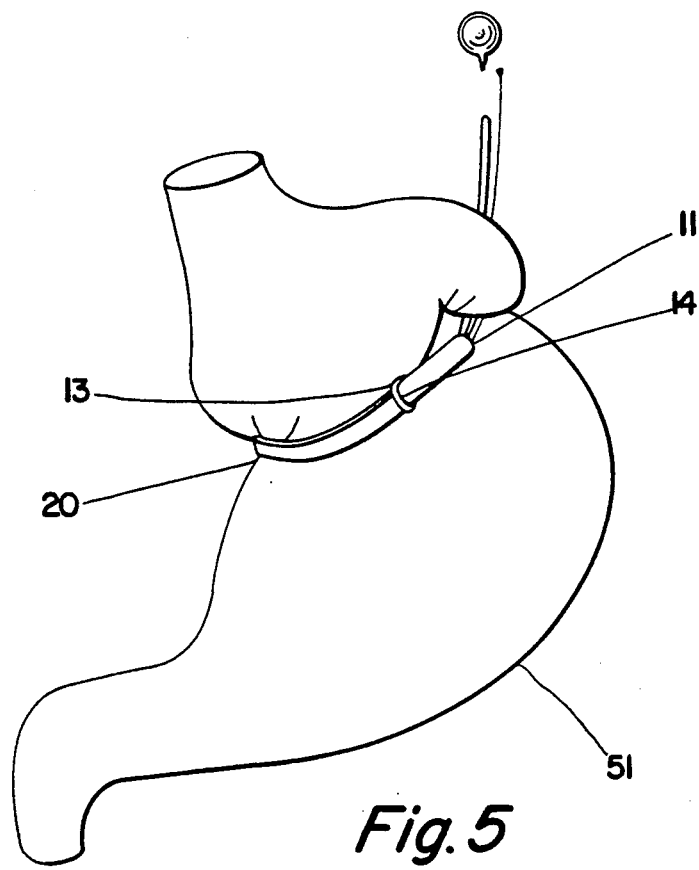
FIG. 5 is a perspective view of the reversible gastric banding device being initially placed in position around a stomach.

The functional relationship of the various portions of the reversible gastric band may be understood by turning now to FIG. 4A which is a perspective view of the reversible gastric band (20) of FIG. 2 with the balloon-like portion (15) inflated for clarity. A pull cord (26) extends from an injection port (not shown) collinearly with the balloon fill tube (17) through a double lumen tubing (41) to terminate at the suture-cutting portion where it is attached to the cutting blade (25). In FIG. 4B, the reversible band (20) end tab (11) is brought through the buckle slot (14) to overlap the band upon itself. A suture (32) is passed through the suture hole (18) then through the overlapping portion of the band (12) and tied off thereby securing the band in a circle. Since the suture(s) (32) secure the band in a circle, the buckle (13) may then be cut off as it is not needed.

Figure 6:
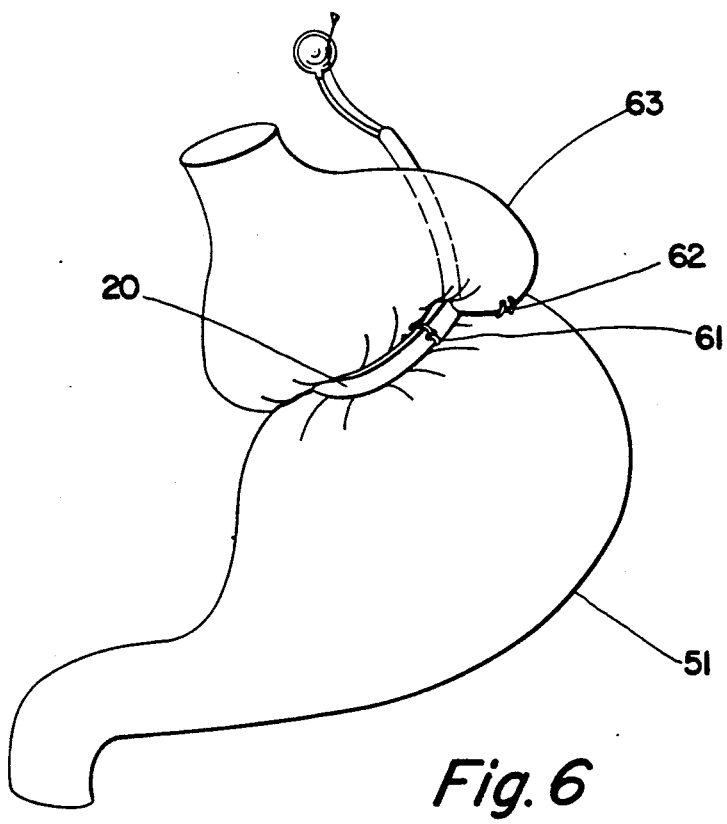
FIG. 6 is a perspective view of the reversible gastric banding device in place after suturing of the greater curvature to retain the device and removal of the buckle.

The use of a reversible gastric band may be best understood by turning now to FIG. (5). The reversible gastric band (20) is first wrapped around the stomach (51) and the guide tab (11) passed through the slot (14) in the buckle (13) and cinched tight until a calibrating apparatus in the stomach (not shown), such as that described in U.S. Pat. No. 4,696,288, indicates the stoma opening, that is, the opening inside the stomach in the portion of the stomach encircled by the band, is the correct size. The loose end of the band (the end of the band that has been passed through the slot in the buckle) is then sutured (61) (FIG. 6) to the band distal to the buckle through the suture guide hole (18) thereby anchoring the band around the stomach. Preferably the suture is 00 Ethabond applied with a non-cutting needle. A small amount of fluid is normally present in the expandable portion of the band (FIG. 2(15)) to facilitate non-surgical enlargement of the stoma opening should it be necessary. The protruding portions of the buckle (13)

may then be cut off and removed. The suture (FIG. 6)(61)) should be non-absorbable and of sufficient strength to hold the band securely about the stomach and capable of resisting expansion as food moves through the stoma opening. FIG. 6 shows the band (20) in place with the buckle (13) removed and secured by a suture (61).

To prevent the reversible gastric band (20) from moving out of position by slipping along the greater curvature of the stomach, the reversible gastric band (20) is retained in position by suturing the greater curvature (51) of the stomach on both sides of the band portion (20) to itself with several sutures (62). The retaining of the banding device (20) in position is important since the size of the upper portion (63) of the stomach determines the amount of food that the patient will consume to achieve satiety. Movement of the band will change the size of the upper portion (63). The stoma opening regulates the flow of food from the upper portion of the stomach to the lower portion of the stomach and consequently controls the rate of ingestion by the patient.

If the patient is ingesting too much food, the expandable balloon-like section of the band (FIG. 4A)(15)) may be expanded to decrease the size of the stoma opening via percutaneous injection of fluid into the expandable portion by means of the implanted injection port (16). Withdrawal of fluid will deflate the device thereby increasing the stoma opening.

The band retaining suture(s) (61) lie directly in the path of the cutting blade (25). The blade pull-cord (26) is conveniently implanted collinearly with the injection port tubing (17) to terminate subcutaneously adjacent the injection port (16). To remove the band from the stomach, the distal end of the pull-cord is located via an incision exposing the injection port. The distal end of the pull-cord is then retracted causing the suture cutting blade (25) to slide in the slot (31) in the direction of tension thereby severing the retaining suture(s) (5) lying in the blade path. The band may then be removed by pulling it out with the injection port.

In practice, it is important to design the reversible gastric band so that the fill tube and the remotely actuated releasing pull-cord are (a) collinear or nearly collinear; and (b) emerge from the gastric band at or near the buckle or guide tab. The collinearity is conveniently achieved by housing the fill tube and pull-cord in double-lumen tubing. The latter feature is readily achieved by having the fill tube and the pull cord emerge either from the guide tab as shown or from the band on either side of the slot in the buckle or from the guide tab as shown in the preferred embodiment. The latter is easily accomplished by narrowing the guide tab end of the gastric band distal to the suture-cutting means so that the buckle slot may be narrowed to accommodate the narrower guide tab end.

There are innumerable possible embodiments which are capable of being remotely actuated to release a reversible gastric band. The suture-cutting devices of FIG. 3A and FIG. 3C are presented as examples only. It is clear that a cotter-type of pin could be used (instead of sutures) to secure the band to itself. The pin could be retracted by remote actuation of a pull wire to free the band. The essence of this invention is not the means used to remotely release a gastric band. The essence of the invention is making the gastric band reversible. Specific embodiments for endowing the gastric band with reversibility as presented herein, are exemplary and are not to limit the scope of the invention.

Although the present invention has been described with reference to preferred embodiments, workers skilled in the art will recognize that changes may be made in form and detail without departing from the spirit and scope of the invention.

What I claim is:

1. A reversible gastric banding device for regulating the size of a stoma opening in a stomach comprising:
   a) a longitudinal flexible substantially non-extensible band portion for encircling the stomach and for partitioning the stomach into a smaller upper portion and a larger lower portion; and
   b) means for securing said band in an encircling position around the stomach;
   c) means for releasing said means for securing said band from its said encircling position around the stomach;
   d) means for actuating said releasing means, said means for actuating being implantable beneath the skin and in material connection with said releasing means.

2. The device of claim 1 further comprising an expandable section located on the band portion adapted for positioning against a stomach wall; and injection site means in fluid communication with the expandable section wherein the expandable section is expandable or deflatable to decrease or increase the size of the stoma opening by addition or withdrawal of fluid through the injection site means.

3. The reversible gastric banding device according to claim 1 wherein said securing means comprises at least one suture.

4. The reversible gastric band according to claim 3 wherein said releasing means comprises a suture cutting blade.

5. The reversible gastric band according to claim 1 wherein said actuator means comprises a longitudinal member which member, in operation, and after implantation, extends from a point beneath the skin to said releasing means affixed to said gastric band.

6. The reversible gastric band according to claim 5 wherein said longitudinal member comprises a wire.

7. The reversible gastric band according to claim 5 wherein said securing means comprises at least one suture.

8. The reversible gastric band according to claim 7 wherein said releasing means comprises a suture cutting blade.

* * * * *